(12) United States Patent
Baker et al.

(10) Patent No.: US 11,270,604 B2
(45) Date of Patent: *Mar. 8, 2022

(54) RESETTABLE SHIELD-ACTIVATED INJECTION DEVICE TRAINER

(71) Applicant: NOBLE INTERNATIONAL, INC., Orlando, FL (US)

(72) Inventors: Jeff Baker, Orlando, FL (US); Wai Yin Christopher Chung, Orlando, FL (US); Shishuang Hou, Ningbo (CN); Francis Michael Siemer, Orlando, FL (US)

(73) Assignee: NOBLE INTERNATIONAL, INC., Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/735,015

(22) Filed: Jan. 6, 2020

(65) Prior Publication Data
US 2020/0143707 A1 May 7, 2020

Related U.S. Application Data

(63) Continuation of application No. 14/945,790, filed on Nov. 19, 2015, now Pat. No. 10,529,252.

(51) Int. Cl.
*G09B 23/28* (2006.01)
*A61M 5/32* (2006.01)
*A61M 5/315* (2006.01)

(52) U.S. Cl.
CPC ....... *G09B 23/285* (2013.01); *A61M 5/31513* (2013.01); *A61M 5/326* (2013.01);
(Continued)

(58) Field of Classification Search
CPC ............ G09B 23/285; A61M 5/31513; A61M 5/3257; A61M 5/326; A61M 5/3287; A61M 2005/3247; A61M 2205/70
(Continued)

(56) References Cited

U.S. PATENT DOCUMENTS 8,062,255 B2 * 11/2011 Brunnberg .......... A61M 5/2033
604/136
8,357,125 B2 * 1/2013 Grunhut .............. A61M 5/2033
604/240
(Continued)

FOREIGN PATENT DOCUMENTS

EP 2784766 A1 10/2014
GB 2493432 A 2/2013
WO 2012003516 A2 1/2012

OTHER PUBLICATIONS

PCT/US2016/062354, International Search Report and Written Opinion, dated Mar. 24, 2017, 10 pages.
(Continued)

*Primary Examiner* — Joseph B Baldori
(74) *Attorney, Agent, or Firm* — Timothy H. Van Dyke; Wolter, Van Dyke, Davis, PLLC

(57) ABSTRACT

In an embodiment, a resettable shield-activated injection training device is provided. The training device includes an outer housing comprising a proximal end and a distal end, an inner housing comprising a proximal end and a distal end, plunger retention protrusions near the proximal end, and an asymmetrical projection at the distal end. The training device may further include a safety shield slidable relative to the outer housing between an extended position and a retracted position, a plunger slidable relative to the outer housing, the plunger comprising one or more plunger rail portions, and a rotatable reset component having axial and radial movement, the reset component comprising a proximal end, a distal end, an outer circumference, and an inner circumference, a notched portion, a plunger rail interface, and an asymmetrical ramped portion in the inner circumference, and a safety shield locking tab near the proximal end of the reset component configured to interact with the safety shield to lock the safety shield in an extended posi-
(Continued)

tion. The training device may further include a reset spring associated with the rotatable reset component, wherein an interaction between the asymmetrical projection and the asymmetrical ramped portion of the reset component causes rotational and axial movement of the reset component toward the proximal end of the outer housing, loads the reset spring, and releases the contact between the safety shield locking tab and the safety shield to unlock the safety shield and reset the device.

14 Claims, 13 Drawing Sheets

(52) U.S. Cl.
CPC ........ *A61M 5/3257* (2013.01); *A61M 5/3287* (2013.01); *A61M 2005/3247* (2013.01); *A61M 2205/70* (2013.01)

(58) Field of Classification Search
USPC .................. 434/262; 604/134, 135, 136, 137
See application file for complete search history.

(56) References Cited

U.S. PATENT DOCUMENTS

| | | | | |
|---|---|---|---|---|
| 8,361,025 B2* | 1/2013 | Lawlis | ............... | A61M 5/31553 604/135 |
| 8,425,460 B2* | 4/2013 | Cowe | ................... | A61M 5/326 604/110 |
| 8,801,674 B2* | 8/2014 | Rolfe | .................. | A61M 5/2033 604/198 |
| 9,033,934 B2* | 5/2015 | Karlsson | ........... | A61M 5/31548 604/197 |
| 9,205,195 B2* | 12/2015 | Burren | .............. | A61M 5/31535 |
| 9,220,847 B2* | 12/2015 | Holmqvist | .......... | A61M 5/2033 |
| 9,242,053 B2 | 1/2016 | Wozencroft | | |
| 10,529,252 B2* | 1/2020 | Baker | .................. | G09B 23/285 |
| 2006/0189938 A1* | 8/2006 | Hommann | .......... | A61M 5/2033 604/137 |
| 2012/0265136 A1 | 10/2012 | Lawlis et al. | | |
| 2013/0053789 A1 | 2/2013 | Harms et al. | | |
| 2013/0236872 A1* | 9/2013 | Laurusonis | .......... | G09B 23/285 434/262 |
| 2014/0221974 A1* | 8/2014 | Bechmann | .......... | A61M 5/2033 604/506 |
| 2014/0288529 A1* | 9/2014 | Baker | ............... | A61M 5/14212 604/506 |
| 2015/0037772 A1 | 2/2015 | Julian et al. | | |
| 2015/0367072 A1* | 12/2015 | Constantineau | .... | A61M 5/3293 604/518 |
| 2016/0175524 A1* | 6/2016 | Henderson | .......... | A61M 5/3204 604/506 |

OTHER PUBLICATIONS

Extended European Search Report in European Application No. 16867074.3, dated May 13, 2019.

* cited by examiner

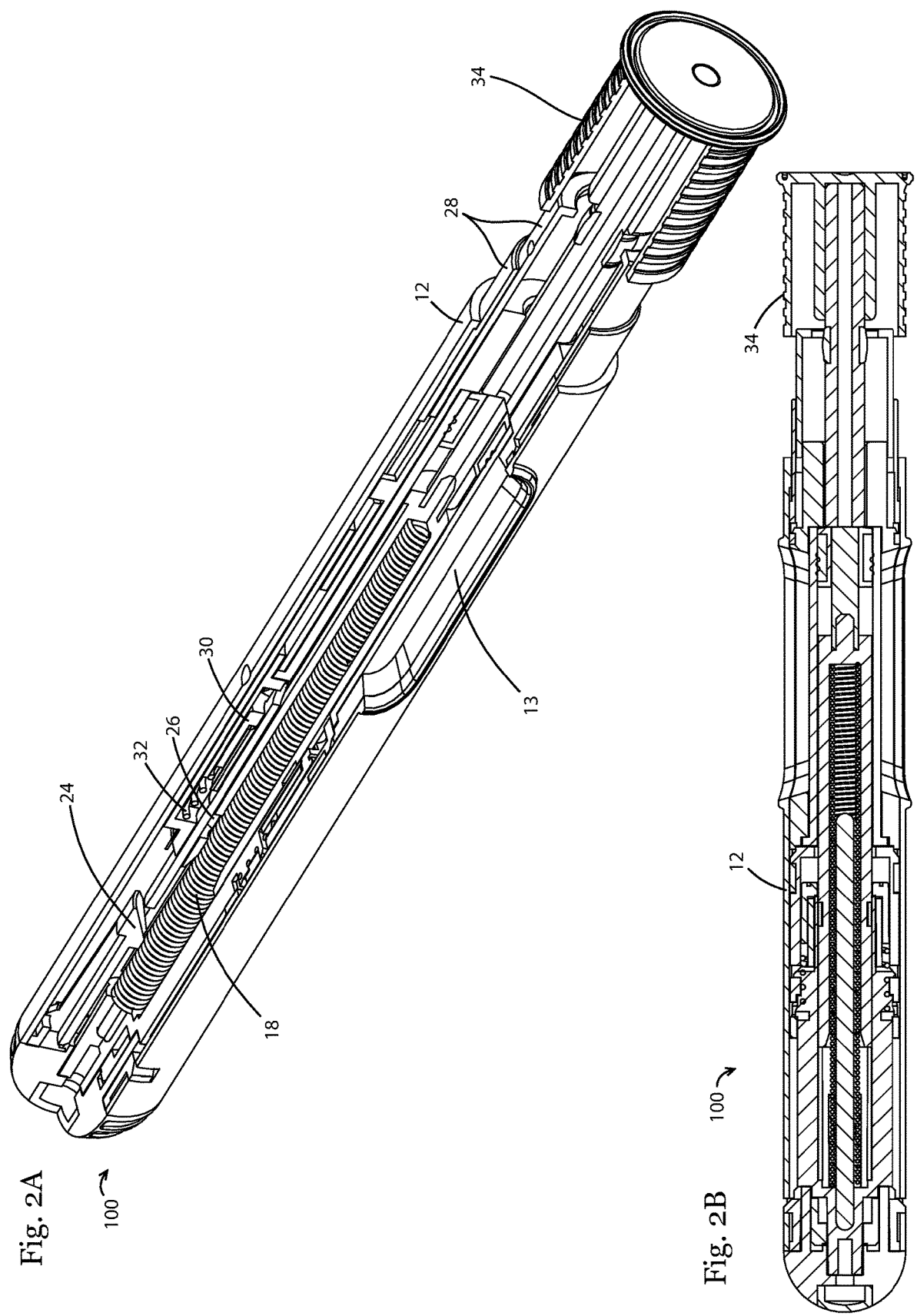

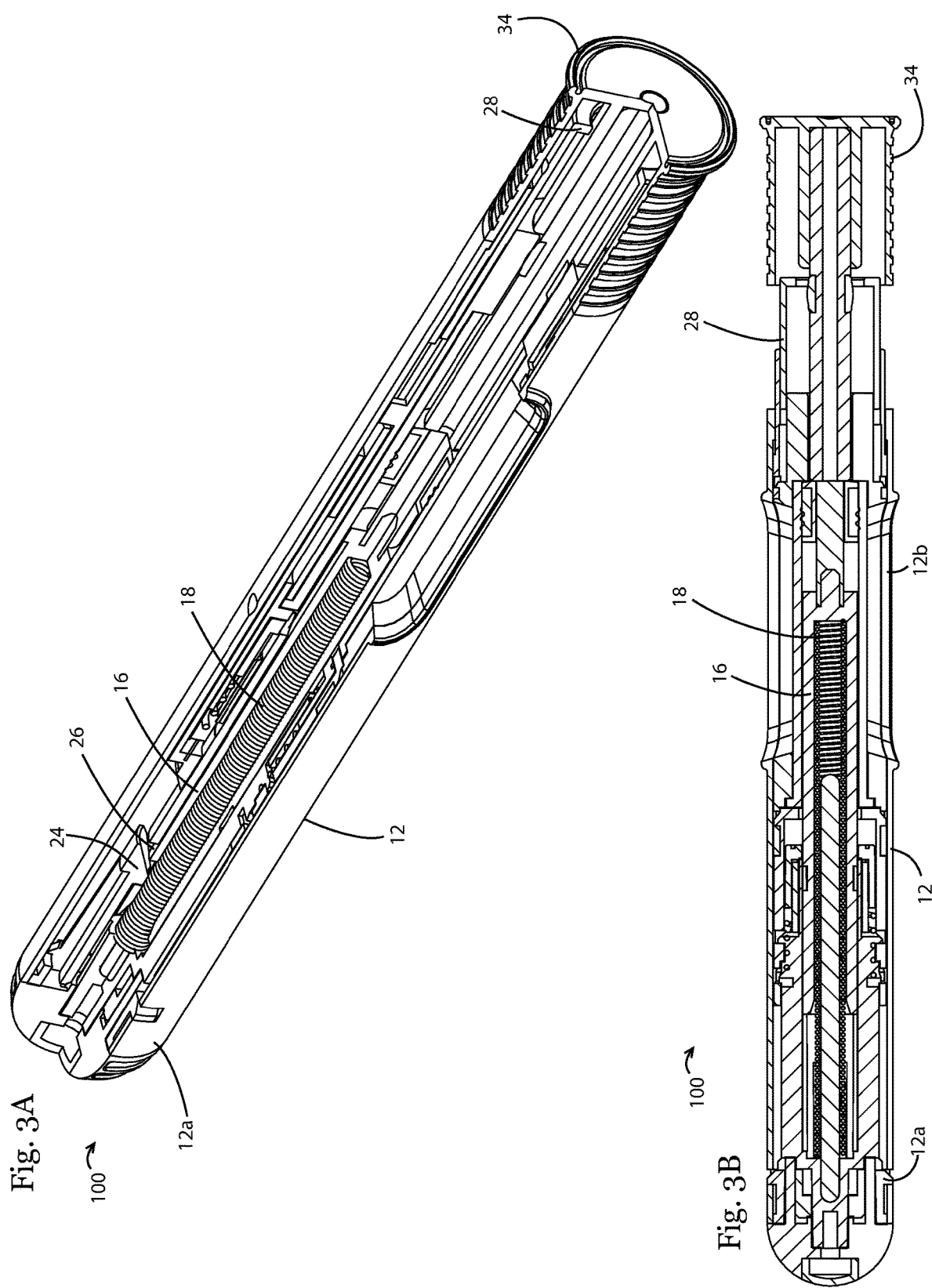

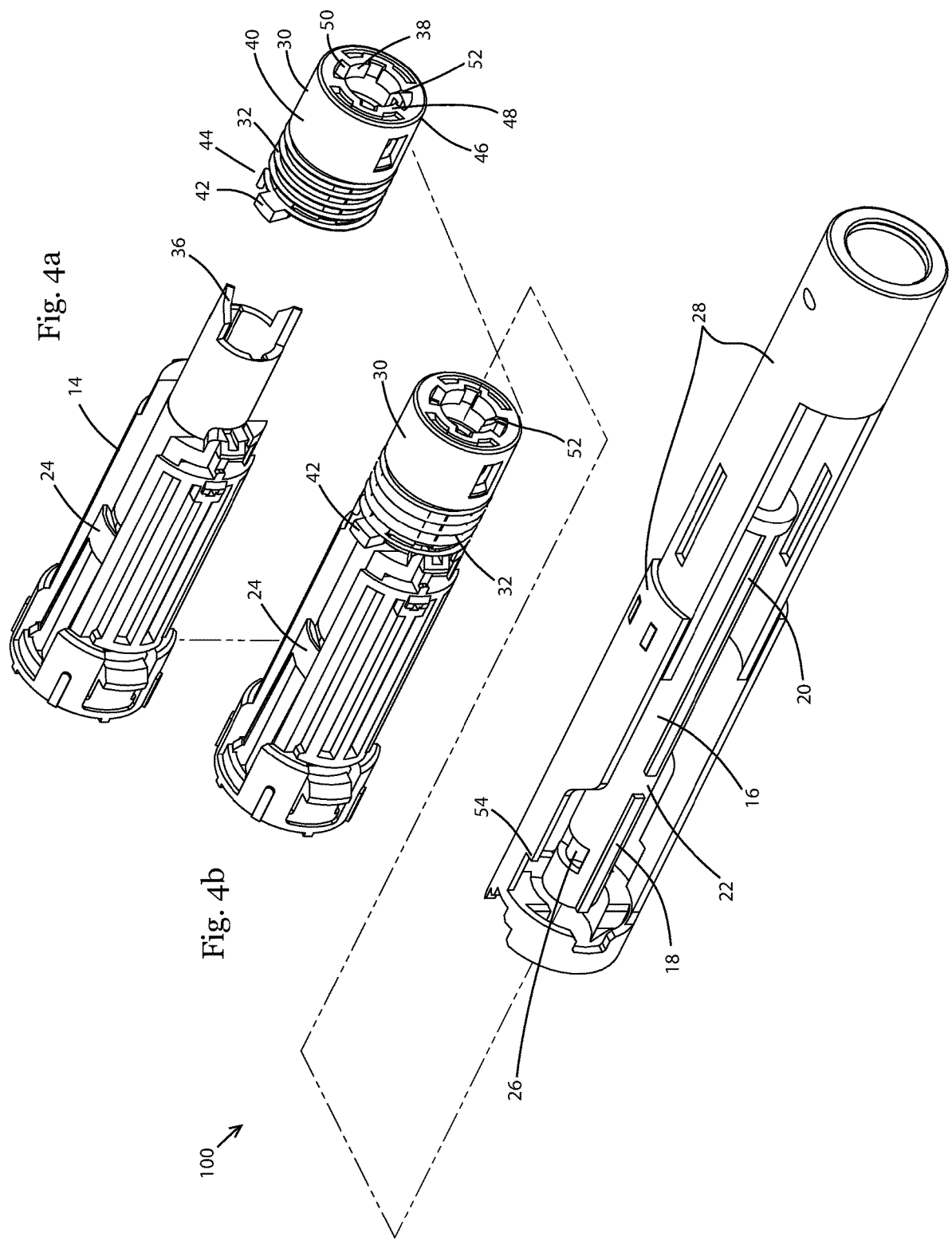

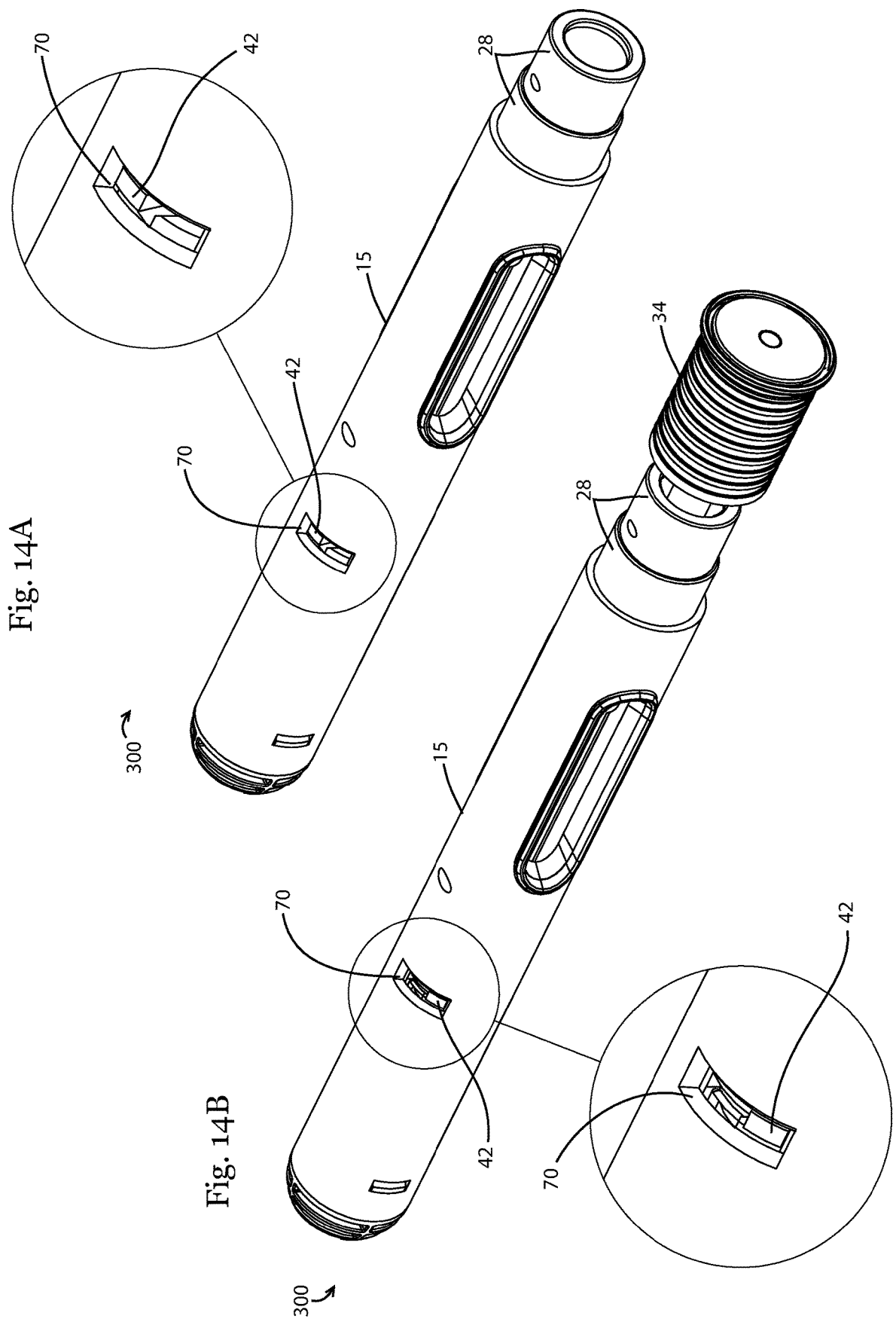

RESETTABLE SHIELD-ACTIVATED INJECTION DEVICE TRAINER

BACKGROUND

Injection devices have recently become increasingly popular for single dose or multi-dose, at home self-administration. These devices include both auto-injection devices and pre-filled syringe devices, and are often designed to accomplish two basic objectives: convenience of drug delivery in an outpatient or at home setting, and/or automation of drug delivery in an outpatient or at-home setting.

Injectable medications are required for a number of varying illnesses and diseases. A number of injectable medications require self-injection by a patient. Self-injection of a medicament using a device having a needle carries with it a certain stigma. Oftentimes patients are weary of injecting themselves for fear or anxiety related to failing to receive a complete dose of the medication, pain associated with injecting oneself with the needle, accidentally sticking oneself with the needle, and difficulties in adequately grasping the dosing mechanism to inject oneself, among other concerns. These fears and anxieties associated with the currently available self-injection devices may result in the administration of an incomplete dose of a medicament, failure to administer any portion of the dose of a medicament, or accidentally sticking oneself with the needle of the device, which in some instances could lead to unwanted transmission of diseases if the needle is contaminated.

An additional concern exists with regard to injection devices is that users with little or no medical knowledge or experience are injecting themselves or injecting others using these devices. Performing a medical treatment or test on oneself or others carries with it certain risks and often creates a level of anxiety for the user performing the treatment or test. It has proven beneficial in the medical field to practice various medical techniques including drug delivery, specifically where it relates to injections and other invasive drug delivery means prior to delivering the medications to a patient in need, and particularly in the case of self-administration of medicaments. Training devices are helpful in reducing anxiety associated with self administering medical treatment, as well as increasing efficiency and accuracy in providing the treatment to patients. Medical devices can be intimidating to use; the fear associated with giving oneself an injection, for example, can be traumatic. This fear is increased in persons with little or no experience in self-administration of medications. Consequently, devices to assist in training individuals to inject themselves or otherwise self-administer medication are beneficial in decreasing or preventing the anxiety associated with medicament delivery. Safe use and re-use of these training devices requires a resettable device. Therefore, a device which allows repeated practice and ease of use to enhance familiarity with the injection device and the self-injection process, along with the ability to safely and efficiently reset the device is paramount to an effective device for injection training.

SUMMARY

In an embodiment, a resettable shield-activated injection training device is provided, including an outer housing comprising a proximal end and a distal end, a plunger slidable relative to the outer housing between a retracted position and an extended position, and a safety shield comprising an extended locked position, an extended unlocked position, and a retracted position, the safety shield being slidable relative to the outer housing between an extended position and a retracted position. The device further includes a rotatable reset component, the reset component configured to mechanically interact with the safety shield, such that when the reset component rotates, the safety shield is unlocked.

In another embodiment, a resettable shield-activated injection training device includes an outer housing having a proximal end and a distal end, a plunger slidable relative to the outer housing between a retracted position and an extended position, and a safety shield comprising an extended locked position, an extended unlocked position, and a retracted position, the safety shield being slidable relative to the outer housing between an extended position and a retracted position, wherein when the safety shield is in the extended locked position, an application of an axial force on the plunger toward the proximal end of the outer housing unlocks the safety shield and resets the device.

In yet another embodiment, a resettable shield-activated injection training device is provided. The training device includes an outer housing comprising a proximal end and a distal end, an inner housing comprising a proximal end and a distal end, plunger retention protrusions near the proximal end, and an asymmetrical projection at the distal end. The training device may further include a safety shield slidable relative to the outer housing between an extended position and a retracted position, a plunger slidable relative to the outer housing, the plunger comprising one or more plunger rail portions, and a rotatable reset component having axial and radial movement, the reset component comprising a proximal end, a distal end, an outer circumference, and an inner circumference, a notched portion, a plunger rail interface, and an asymmetrical ramped portion in the inner circumference, and a safety shield locking tab near the proximal end of the reset component configured to interact with the safety shield to lock the safety shield in an extended position. The training device may further include a reset spring associated with the rotatable reset component, wherein an interaction between the asymmetrical projection and the asymmetrical ramped portion of the reset component causes rotational and axial movement of the reset component toward the proximal end of the outer housing, loads the reset spring, and releases the contact between the safety shield locking tab and the safety shield to unlock the safety shield and reset the device.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which:

FIG. 2A is a partial sectional view of the embodiment of the device shown in FIG. 1A in a mid-reset position, with a reset cap associated at a distal end of the device.

FIG. 2B is a cross-sectional view of the embodiment of the device shown in FIG. 2A.

FIG. 3A is a partial sectional view of the embodiment of the device shown in FIG. 1A in a reset position with a reset cap on the distal end of the device.

FIG. 3B is a cross sectional view of the embodiment of the device shown in FIG. 3B.

FIG. 4a is a further exploded view of internal components of the components in the embodiment of the device shown in FIG. 4b.

FIG. 4b is an exploded view of internal components of an embodiment of the device.

FIGS. 14A-B include perspective views of another embodiment of a resettable shield-activated injection training device.

DETAILED DESCRIPTION

Figures 1A, 1B:
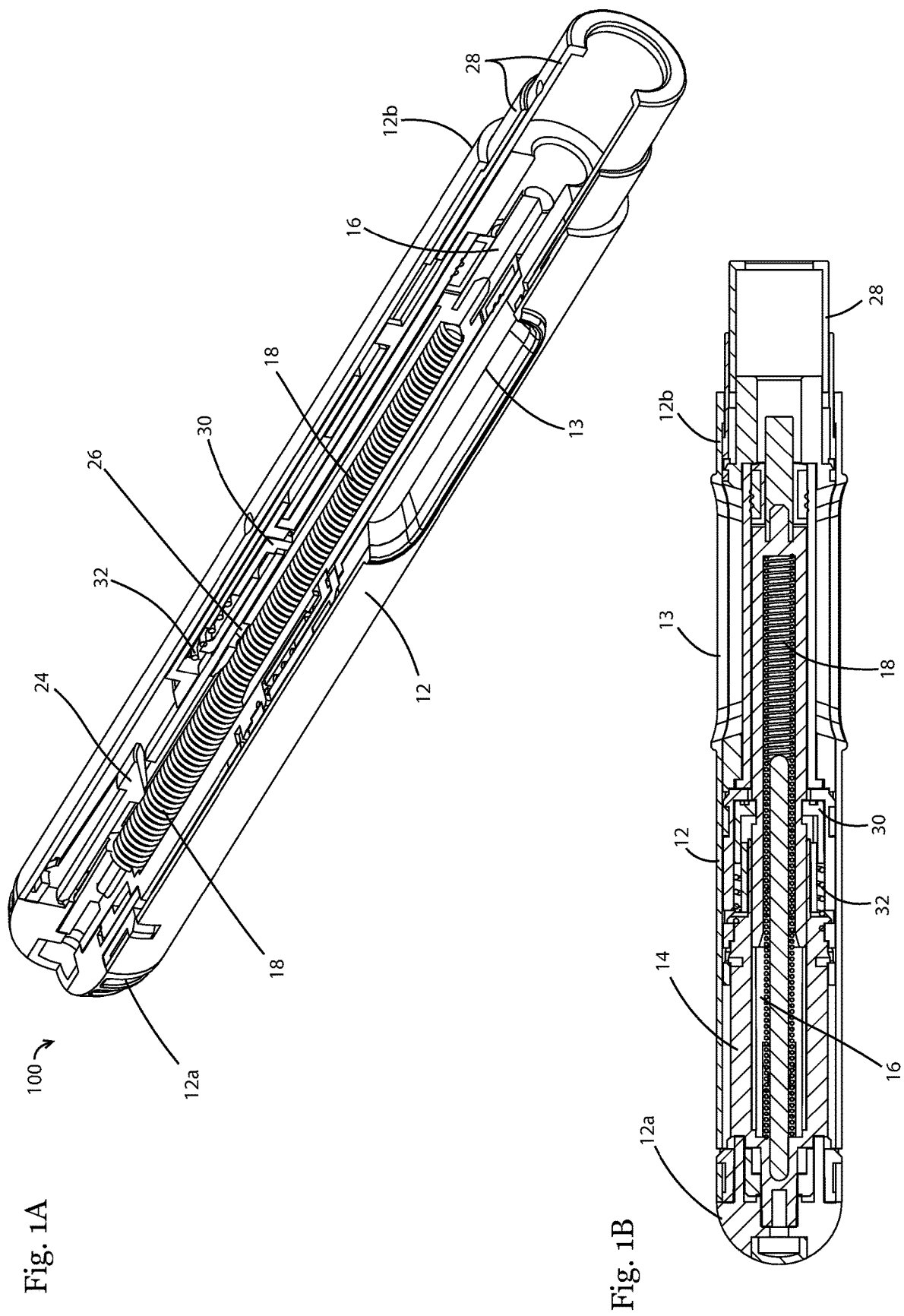
FIG. 1A is a partial sectional view of an embodiment of the resettable shield-activated injection training device in a "fired: position.
FIG. 1B is a cross sectional view of the resettable shield activated injection training device embodiment shown in FIG. 1A.

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another. The modifier "about" used in connection with a quantity is inclusive of the stated value and has the meaning dictated by the context. It is to be noted that all ranges disclosed within this specification are inclusive and are independently combinable.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. As a non-limiting example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 7. As another non-limiting example, a range of "between 20 and 10" can also include the values 20, 10.

The term "adjacent" as used herein, includes but is not limited to near, associated with, or in close proximity to.

In an embodiment, a resettable shield-activated injection training device is provided. The device may include an outer housing having a proximal end and a distal end, an inner housing including a proximal end and a distal end, plunger retention protrusions near the proximal end, and an asymmetrical projection at the distal end. The device may further include a safety shield slidable relative to the outer housing between an extended position and a retracted position, a plunger slidable relative to the outer housing, the plunger comprising one or more plunger rail portions, a rotatable reset component having axial and radial movement, the reset component comprising a proximal end, a distal end, an outer circumference, and an inner circumference, a notched portion, a plunger rail interface, and an asymmetrical ramped portion in the inner circumference, and a safety shield locking tab near the proximal end of the reset component configured to interact with the safety shield to lock the safety shield in an extended position; and a reset spring associated with the rotatable reset component. An interaction between the asymmetrical projection and the asymmetrical ramped portion of the reset component may cause rotational and axial movement of the reset component toward the proximal end of the outer housing, load the reset spring, and release the contact between the safety shield locking tab and the safety shield to unlock the safety shield and reset the device. In one non-limiting embodiment, the reset spring may include a torsion spring.

In a further embodiment, movement of the reset component toward the distal end of the outer housing causes the asymmetrical ramped portion to interface with the asymmetrical projection of the inner housing, causing the rotational movement of the reset component.

In still a further embodiment, the plunger includes a proximal plunger rail portion and a distal plunger rail portion, wherein the proximal and distal plunger rail portions are aligned along a longitudinal axis of the plunger, and a plunger rail gap is disposed between the proximal plunger rail portion and the distal plunger rail portion.

In yet a further embodiment, the reset component may be rotated until the notch receives the distal plunger rail portion. Further movement of the plunger toward the proximal end of the device causes the distal plunger rail portion to slide within the notch of the reset component to reset the plunger, maintaining the reset spring in a loaded position, until the plunger retention protrusions engage with an opening at the distal end of the plunger to retain the plunger in a pre-fired position. Movement of the unlocked shield toward the proximal end of the outer housing causes the plunger to move toward the distal end of the housing to fire the device.

An alignment between the notch and/or plunger rail interface of the reset component with the plunger rail gap allows the reset spring to unload, and the reset component to rotate such that the safety shield locking tab interacts with the safety shield, to lock the safety shield in an extended position. When the safety shield is in an extended, locked position, the distal plunger rail portion and/or the proximal plunger rail portion is aligned with the plunger rail interface of the reset component, such that movement of the plunger toward the proximal end of the device is prevented.

In a further embodiment, the device may include a reset cap, the reset cap having a distal end portion and a reset rod configured to interface with the plunger to reset the device.

In yet a further embodiment, the plunger may include a plunger spring, wherein the plunger spring is configured to move the plunger toward the distal end of the outer housing when the device is activated.

Turning to the Figures, FIGS. 1A and 1B show a partial sectional view, and a cross sectional view, respectively, of an embodiment of a resettable shield-activated injection training device 100 in a fired position. The device 100 includes an outer housing 12 having a proximal end 12a and a distal end 12b, an inner housing 14, a plunger 16 slidable relative to the outer housing, a viewing window 13 in the outer housing providing a user a view into the device. The viewing window may allow a user to see whether the device has been fired, or whether it has been reset for a subsequent use, as it may provide a view of the plunger 16 location through the outer housing 12 of the device 100. A plunger spring 18 is visible in the sectional view of FIG. 1A, the plunger spring 18 is provided to deliver the plunger 16 toward the distal end of the housing once the device 100 has been activated. The plunger 16 further includes a proximal plunger rail portion 18 and a distal plunger rail portion 20 (not shown in FIG. 1A-B), wherein the rail portions are aligned along the longitudinal axis of the device 100. A plunger rail gap 22 (not shown in FIG. 1A-B) is disposed between the proximal and distal plunger rail portions 18, 20. In other non-limiting embodiments, additional rail portions and additional gaps may be provided in addition those described herein. One or more plunger retention protrusions 24 are provided near the proximal end of the device 100, and a plunger opening 26 is provided in the plunger 16. The plunger opening 26 is provided to receive the plunger retention protrusion 24 when the plunger 16 is in a fully reset position (shown in FIG. 3A).

In the fired position shown in FIGS. 1A-1B, a safety shield 28 is shown in an extended, locked position. A reset component 30 is also provided, along with reset spring 32. In a non-limiting embodiment, the reset spring 32 may include a torsion spring. In FIGS. 1A-B, the reset spring 32 is in an unloaded condition, and a safety shield locking tab 42 (not shown in FIGS. 1A-B) portion of the reset component 30 abuts a portion of the safety shield 28 to maintain the safety shield 28 in an extended, locked position after use of the device 100, i.e., in a "fired" position, and until the device is reset for a subsequent use.

During use of the shield-activated device, when the device is in a fully reset position, the safety shield 28 is in an unlocked condition, the safety shield locking tab does not abut against the locking tab protrusion, and the safety shield 28 may be pressed against a target surface of a user to activate the device 100 and simulate an injection. Once the safety shield 28 is compressed, movement of the plunger 16 toward the distal end of the device 100 may occur to activate the device and simulate an injection event. This operation may occur by compression of the distal end of the safety shield 28 by pressing the safety shield 28 against a target surface, wherein an interface between a proximal end of the safety shield 28 and the one or more plunger retention protrusions 24 causes the plunger retention protrusions 24 to be released from the one or more plunger openings 26 such that the plunger spring 18 may be released, forcing the plunger 16 toward the outer housing distal end 12b.

FIG. 2A is a partial sectional view of the embodiment of the device 100 shown in FIG. 1A in a mid-reset position, with a reset cap 34 associated with a distal end of the device 100. FIG. 2B is a cross-sectional view of the embodiment of the device 100 shown in FIG. 2A, also showing reset cap 34 at distal end of the device 100. The reset cap 34 has been partially inserted into the device 100, such that a portion of the reset cap 34 contacts the distal end of the plunger 16, and further movement of the reset cap 34 toward the proximal end of the device 100 moves the plunger 16 toward the outer housing proximal end 12a.

FIG. 3A is a partial sectional view of the embodiment of the device 100 shown in FIG. 1A in a fully reset position with the reset cap 34 on the distal end of the device 100. FIG. 3B is a cross sectional view of the embodiment of the device 100 shown in FIG. 3B. In the views of FIGS. 3A-3B, with the device in a fully reset position, the plunger 16 is near the proximal end of the outer housing 12a, the plunger spring 18 is loaded, and the safety shield 28 is in an unlocked position. The position of the plunger 16 at the proximal end of the outer housing 12a of the device 100, in its fully reset position, allows the plunger opening 26 to be positioned such that the plunger retention protrusions 24 interface with the plunger opening 26 to maintain the plunger in the pre-fired, fully reset position until the device 100 is actuated. Once the reset cap 34 is removed from the device 100, the device 100 can be actuated beginning with the safety shield 2, which can be pressed against a surface (i.e., a target area of a user) forcing movement of the safety shield 28 toward the outer housing proximal end 12a, until the safety shied 28 interfaces with the plunger retention protrusion 24, forcing the plunger retention protrusion 24 from the plunger opening 26.

FIG. 4A and FIG. 4B are exploded views of internal portions of an embodiment of the device 100 including an inner housing 14, configured to associate with the reset component 30. The inner housing 14 may include plunger retention protrusions 24 which extend in toward the center of the inner housing 14. The plunger retention protrusions 24 are configured to associate with a portion of the plunger 16, the plunger opening 26 when the plunger 16 is in a reset position. The inner housing 14 further includes one or more asymmetrical projections 36 at or near its distal end. The asymmetrical projections 36 are configured to interact with a portion of the reset component 30 on an inner circumference 38 thereof. The reset component 30 may include a proximal end 44, a distal end 46, an outer circumference 40, an inner circumference 38, and may include one or more notches 50 in the inner circumference 38. An asymmetrical ramped portion 52 may be provided on the inner circumference 38 of the reset component 30. The asymmetrical ramped portion 52 is provided to interact with the asymmetrical projection 36 of the inner housing 14 during reset of the device 100. Movement of the reset component 30 relative to the inner housing 14, toward the proximal end of the outer housing 12a causes the asymmetrical ramped portion 52 to interact with the asymmetrical projection 36 on the inner housing 14. This interaction causes the reset component 30 to rotate relative to the inner housing 14, biasing, or loading the reset spring 32 until plunger rail portions 18, 20 of the plunger 16 align with the notches 50 on the inner circumference of the reset component 30, wherein which further movement of the plunger 16 toward the proximal end of the outer housing 12a allows the plunger 16 to be fully reset. Once the plunger 16 reaches the outer housing proximal end 12a, the plunger openings 26 (see FIG. 4B) are positioned relative to the plunger retention protrusions 24, such that the plunger retention protrusions 24 can extend into the openings 26 to maintain the plunger 16 in the reset position until the device 100 is fired.

In FIG. 4A the inner housing 14 is dissembled from the reset component 30. In FIG. 4B the inner housing 14 and reset component 30 are assembled together, but the inner housing 14/reset component 30 assembly is removed from the safety shield 28 assembly. Locking tab protrusion 54 can be seen on the safety shield 28 in FIG. 4B. When the device 100 has been fired, and the safety shield 28 is in an extended, locked position, the safety shield locking tab 42 interfaces with the locking tab protrusion 54 to maintain the safety shield 28 in the extended, locked position until reset of the device 100.

Figure 5:
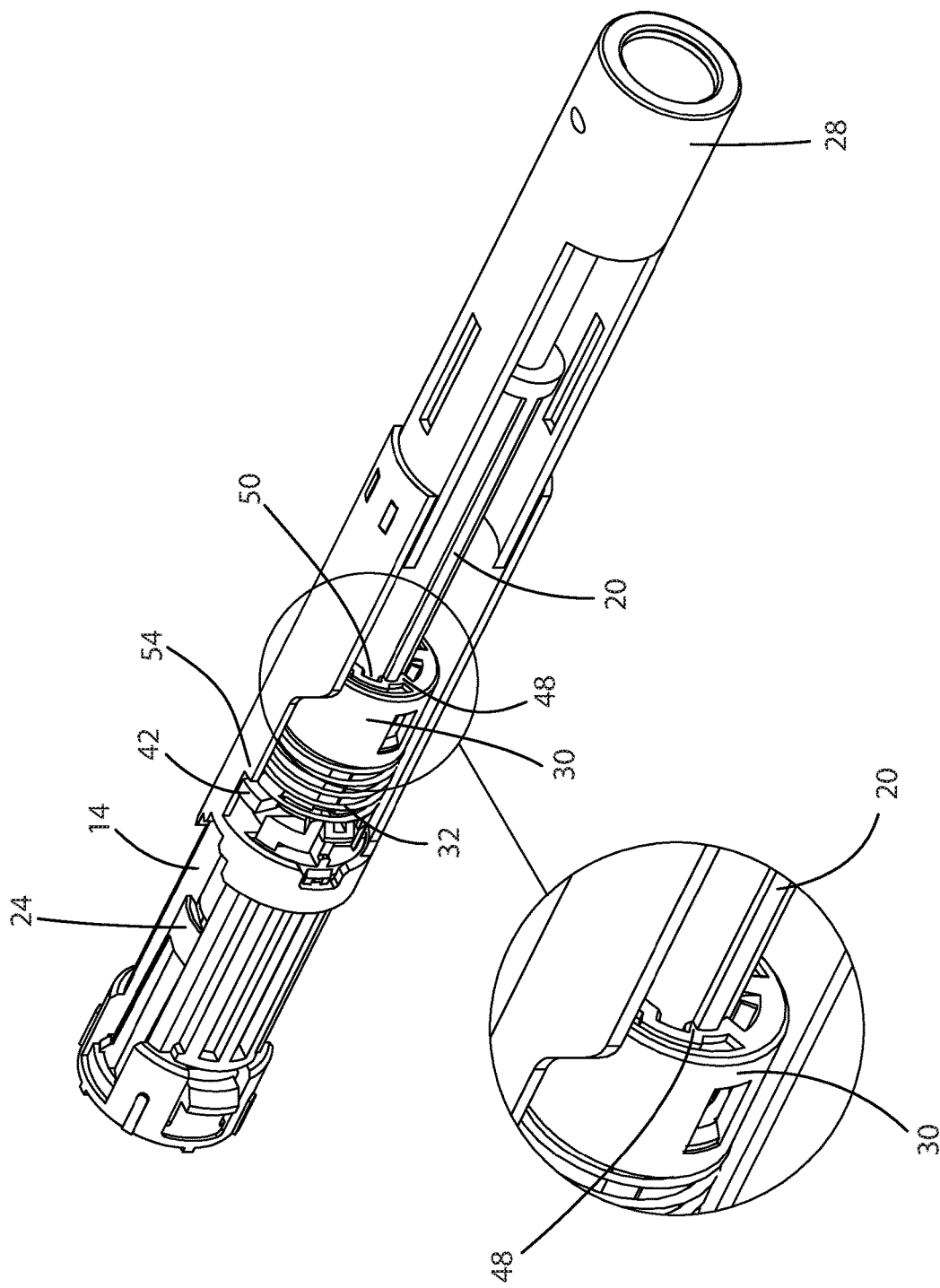
FIG. 5 is an assembled view of the components of the device shown in FIG. 4, wherein the device in FIG. 5 is in a "fired" position.

FIG. 5 is an assembled view of the components of the device 100 shown in FIG. 4, wherein the device in FIG. 5 is in a "fired" position. In FIG. 5, the safety shield locking tab 42 is positioned in contact with the locking tab protrusion 54, so as to maintain the safety shield 28 in an extended, locked position until the device 100 is reset. In order to reset the device 100, the reset cap 34 (not shown in FIG. 5) is inserted into the distal end of the device 100, such that a portion of the reset cap 34 contacts the plunger 16. Movement of the reset cap 34 toward the proximal end of the outer housing 12a (not shown in FIG. 5) moves the plunger toward the proximal end of the outer housing 12a, until the distal plunger rail portion 20 abuts the plunger rail interface 48 of the reset component 30. Further movement of the plunger 16 in this direction forces the reset component 30 to move relative to the inner housing 14 as the asymmetrical ramped portion 52 interfaces with the asymmetrical projection 36 on the inner housing, forcing the reset component to rotate such that the safety shield locking tab 42 moves away from the locking tab protrusion 54 to unlock the safety shield 28 and load the reset spring 32. This rotation continues as the plunger 16 is moved toward the proximal end of the outer housing until the notches 50 of the reset component 30 reach a gap in the plunger rail, i.e., the plunger rail gap 22, at which point the distal plunger rail portion 20 and/or the proximal plunger rail portion 18 may be received within the notch 50, such that the plunger 16 can continue to be reset (i.e., moved in the proximal direction toward the outer housing proximal end 12a). This movement continues as long as reset cap is inserted into the device 100 until the plunger proximal end reaches a point in which the plunger opening 26 receives the plunger retention protrusion 24. The plunger retention protrusion 24 may be biased inward, such that when the plunger 16 is at a position in which the plunger opening 26 is adjacent to the plunger retention protrusion 24, the protrusion 24 traverses the plunger opening 26. More than one plunger retention protrusion 24 may be provided, and a corresponding more than one plunger opening 26 may be provided on the device 100. The plunger retention protrusion(s) 24 may include a tab portion on the inner surface such that the tab portion retains the plunger 16 in the reset position by way of its association with the plunger opening 26. FIG. 5 also includes a close-up view of the reset component 30 and distal plunger rail portion 20 as well as the plunger rail interface 48.

FIGS. 6A-B include perspective views of components of the device 100 embodiment shown in FIG. 5 in a position during reset of the device 100. FIG. 6A is a view of the inner housing 14 of the device 100 with the plunger 16 and safety shield 28 removed. FIG. 6A shows the reset component 30 being rotated in a counter-clockwise direction relative to the distal end of the inner housing 14 as described above. The safety shield locking tab 42 is displaced from the locking position shown in FIG. 5, and as provided in FIG. 6B, the rotatable component 30 has been rotated such that it is not in contact with the locking tab protrusion 54 on the safety shield 28. This rotation of the reset component 30 and consequently, the rotation of the safety shield locking tab 42 away from the locking tab protrusion 54 releases the safety shield 28 from an extended locked position to an unlocked position. The rotation of the reset component 30, dependent, in one embodiment upon the interaction between the asymmetrical ramped portion 52 and the asymmetrical projection 36 as the device 100 is being reset to a pre-fired position, loads the reset spring 32. FIG. 6B also includes a zoomed in view of the reset component 30, showing the position of the reset component in relation to the distal plunger rail portion 20 during the reset.

Figure 6:
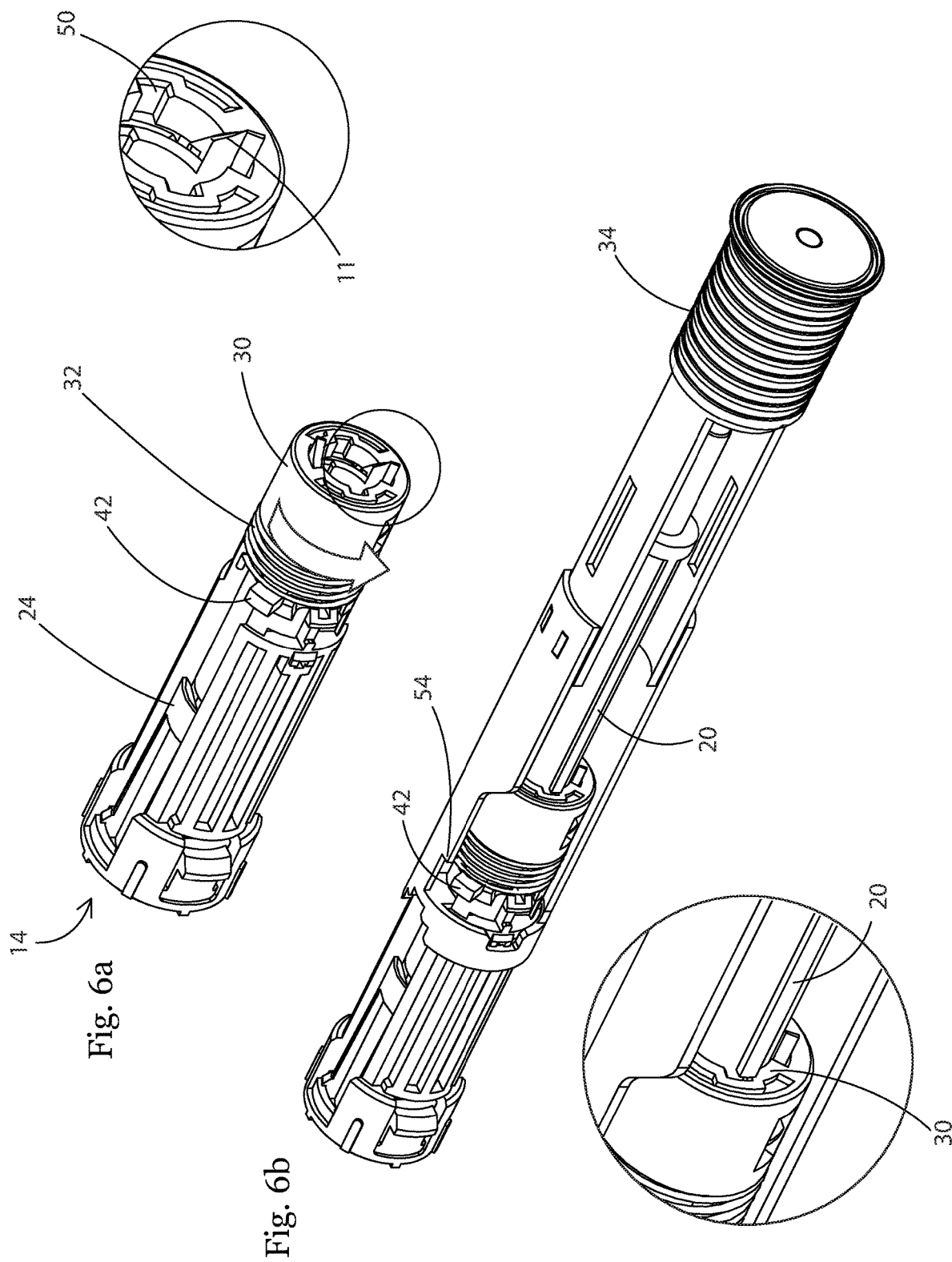
FIG. 6a is a perspective view of a portion of the device embodiment shown in FIG. 5, wherein the device is shown in a mid-reset position.
FIG. 6b is a perspective view of a portion of the device embodiment with the reset cap associated therewith.
Figure 7:
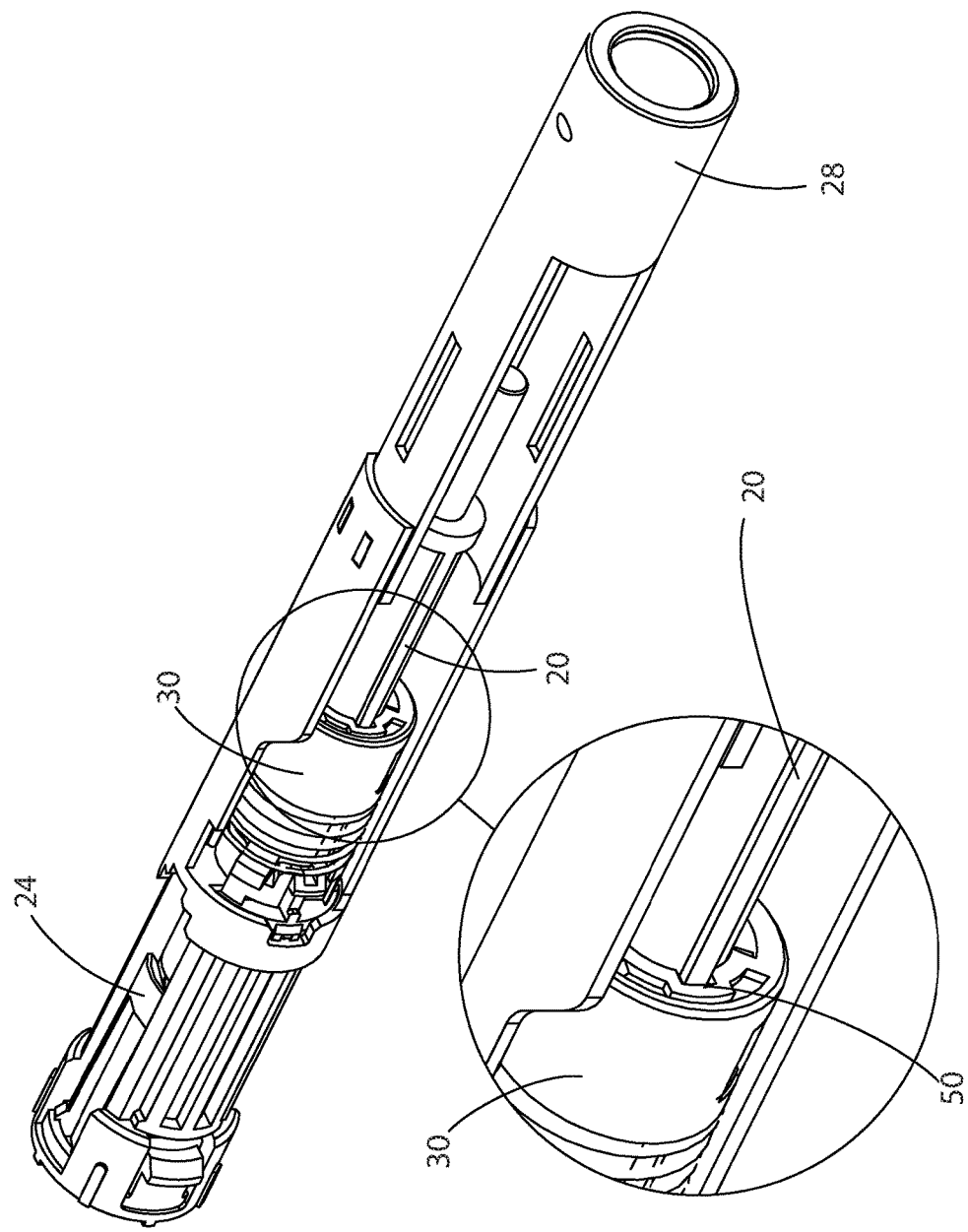
FIG. 7 is a perspective view of the device embodiment shown in FIG. 6, wherein the device is shown in a fully reset position.

FIG. 7 is a perspective view of the device 100 embodiment shown in FIG. 6, in a fully reset position. The distal plunger rail portion 20 slides within the notch 50. Only one distal plunger rail portion 20 is shown in FIG. 7, however, multiple may be provided on the surface of the plunger 16, multiple notches 50 configured to interact with the plunger rail portion 20 may also be provided along the inner circumference 38 of the rotatable component 30. The plunger retention clip 24 is interfacing with the plunger opening 26 on the plunger 16 in the reset position shown in FIG. 7.

Figure 8:
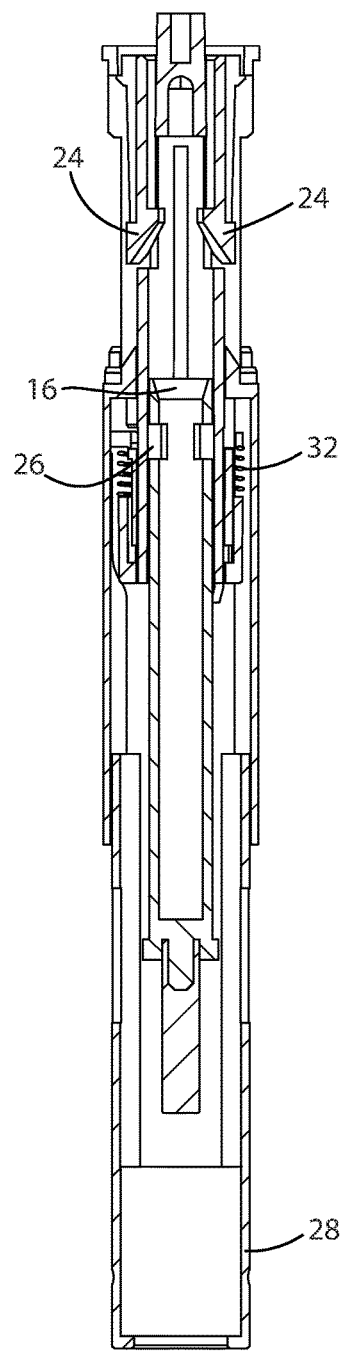
FIG. 8 is a cross sectional view of the device embodiment shown in FIG. 5, in fired position.
Figure 9:
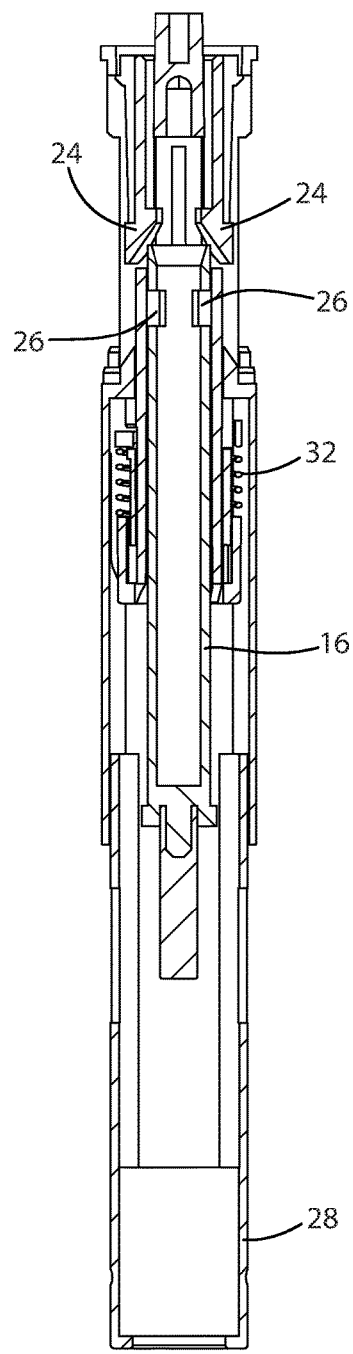
FIG. 9 is a cross sectional view of the device embodiment shown in FIG. 6, in a mid-reset position.
Figure 10:
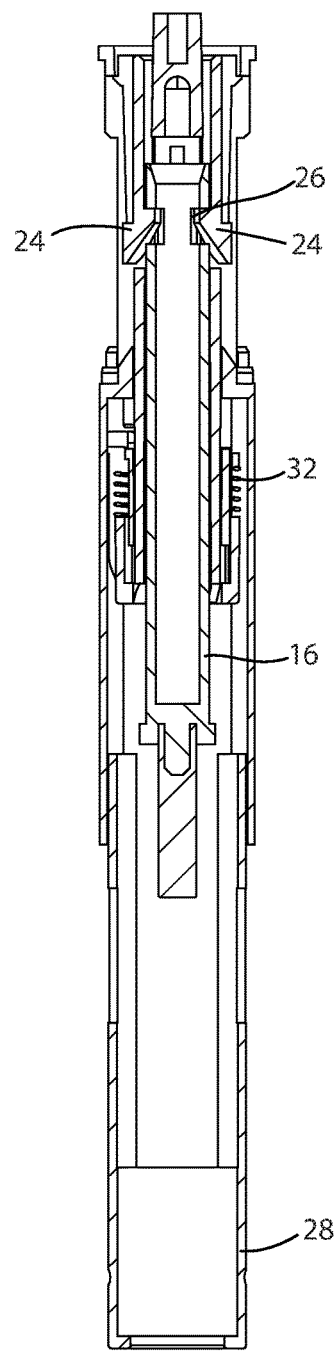
FIG. 10 is a cross sectional view of the device embodiment shown in FIG. 7, in a fully reset position.

FIG. 8 is a cross sectional view of the device 100 embodiment shown in FIG. 5, in fired position, wherein the plunger 16 is in a fired position, wherein the plunger retention clips 24 are not interfacing with the plunger opening 26. The rest spring 32 is in an unloaded position, and the safety shield 28 is in an extended, locked position. FIG. 9 shows a cross sectional view of the device 10 embodiment shown in FIG. 8, during reset, wherein the reset spring 32 is being loaded, the plunger 16 is being moved toward the proximal end of the outer housing 12a (not shown in FIG. 8), and the plunger retention clips 24 are not yet interfacing with the plunger openings 26. Reset cap 34 (not shown in FIG. 9) may be inserted into the distal end of the outer housing through an opening in the safety shield 28, and a portion of the reset cap 34, (in one non-limiting embodiment, a reset rod portion which extends from an inner portion of the cap) may be inserted into the distal end of the outer housing until it reaches the plunger 16. The reset cap 34 maybe used to apply axial force to the plunger to effect rotation of the reset component 30 to unlock/release the safety shield 28 from a locked position and reset the plunger 16. In the cross sectional view of FIG. 10, the device 100 embodiment shown in a fully reset position, wherein the plunger has been reset, i.e., moved toward the proximal end of the device 100 such that the plunger openings 26 interface with the plunger retention protrusions 24 at the proximal end of the device 100. The reset spring 32 is loaded, and the safety shield 28 is in an unlocked position.

Figure 11A:
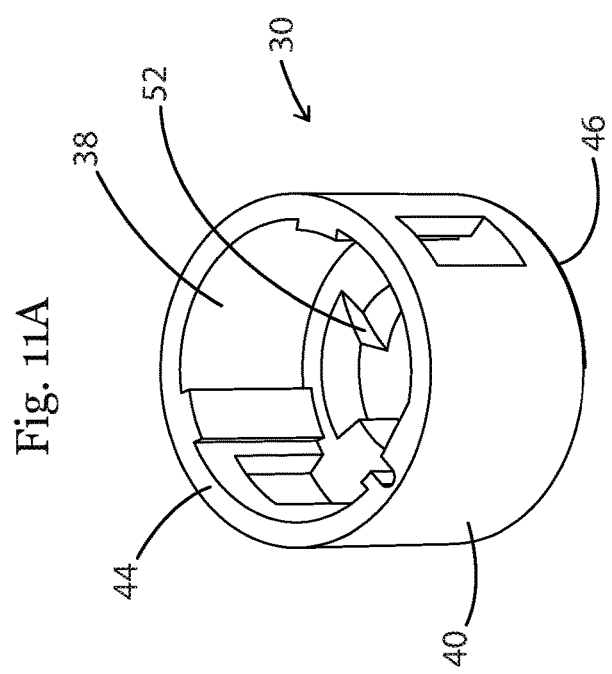
FIGS. 11A-C include perspective, top and cross-sectional views, the cross sectional view was taken at B-B of FIG. 11B of a reset component of an embodiment of the device described herein.
Figure 11C:
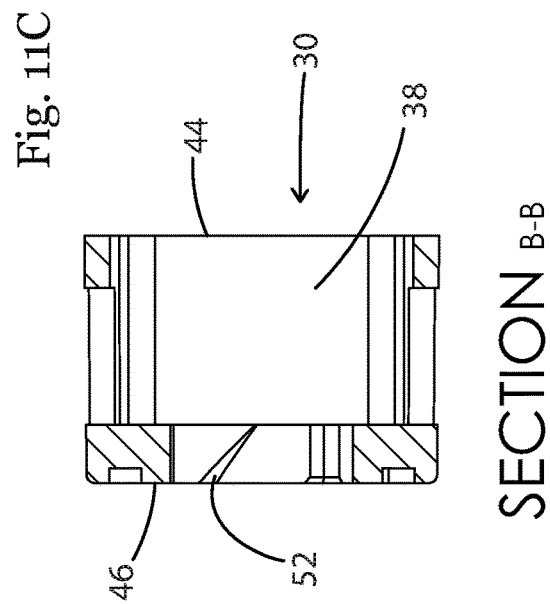
Figure 11B:
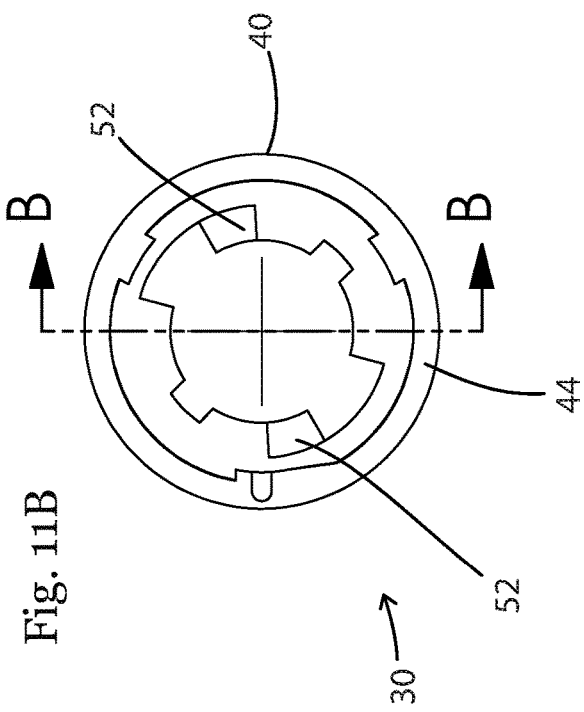

FIGS. 11A-C include perspective, top and cross-sectional views of the reset component 30. The cross sectional view of FIG. 11C was taken at B-B of FIG. 11B. The reset component 30 including the reset component proximal end 44, the reset component distal end 46, the outer circumference 40, and the inner circumference 38 are shown. The asymmetrical ramped portion 52 can be seen in FIG. 11A and FIG. 11C. Two asymmetrical ramped portions 52 are seen in FIG. 11B; however this is not intended to be limiting, there may be one asymmetrical ramped portion 52 or multiple asymmetrical ramped portions 52 on the reset component 30.

Figure 12:
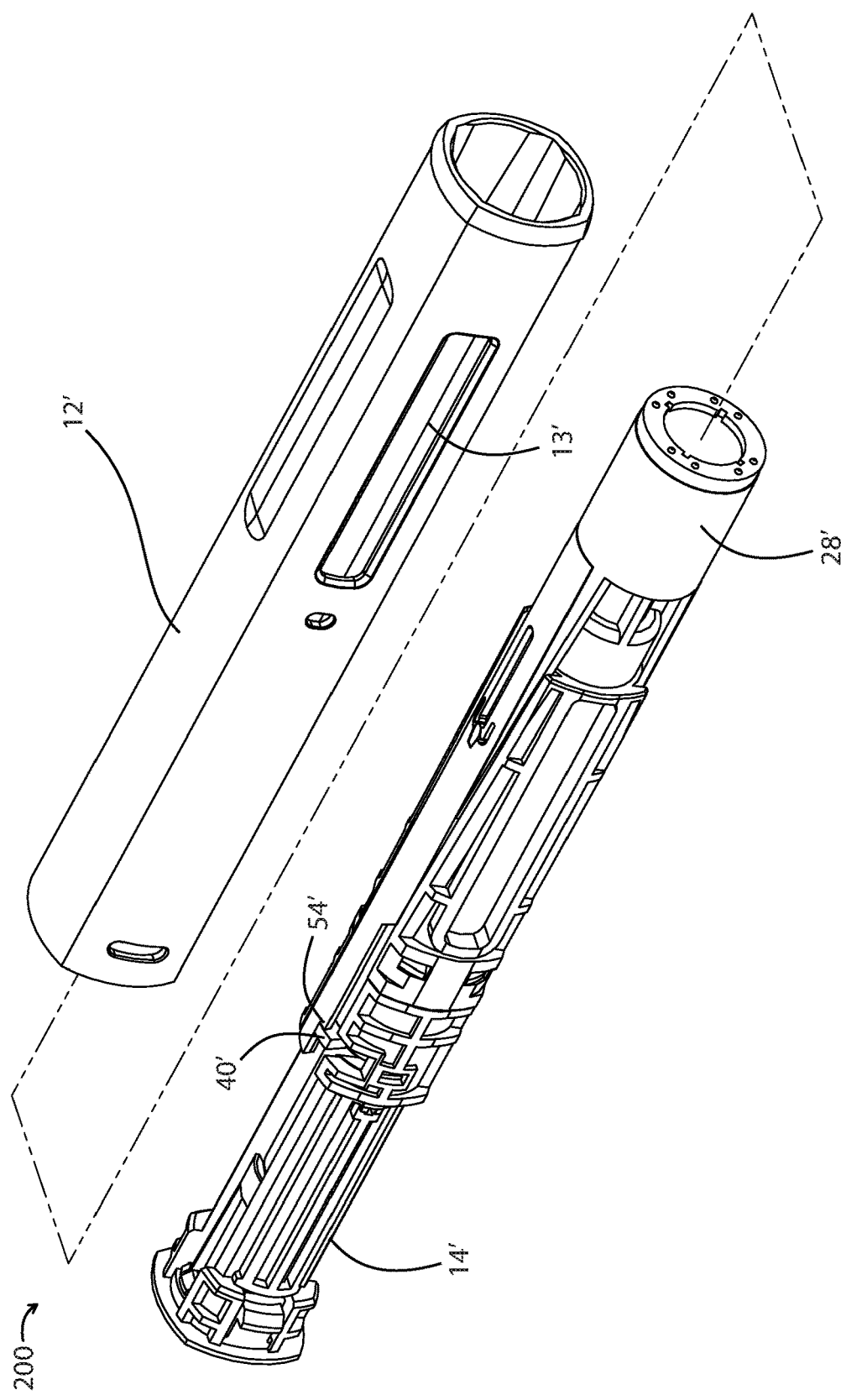
FIG. 12 is a partially exploded view of another embodiment of the resettable shield-activated injection training device in a fired position.
Figure 13:
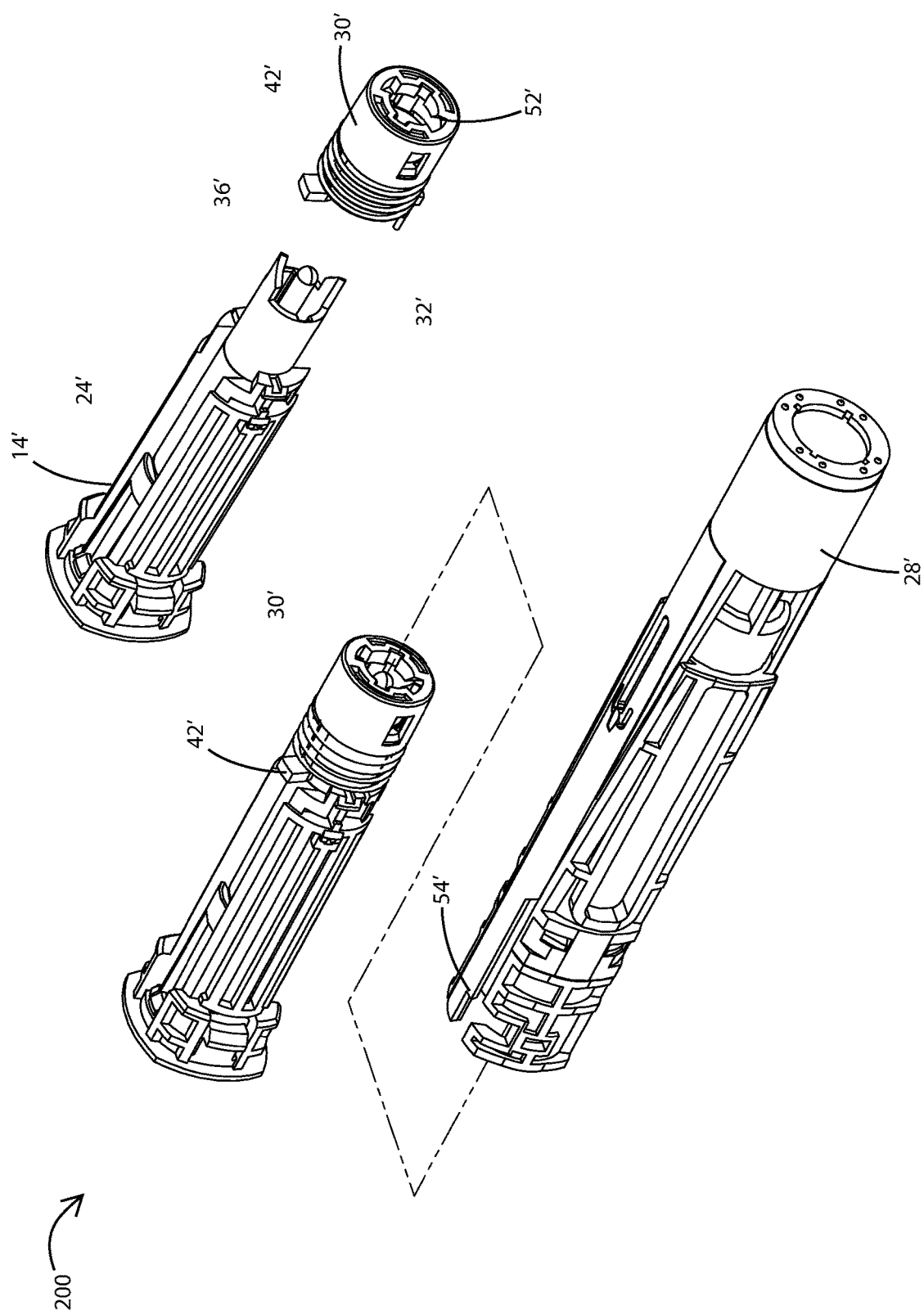
FIG. 13 is an exploded view of the inner housing of the embodiment of the device shown in FIG. 12.

FIG. 12 is a partially exploded view of another embodiment of the resettable shield-activated injection training device 200 in a fired position. The alternative embodiment of the device 200 includes an outer housing 12', an inner housing 14', in one non limiting embodiment. The device 200 further includes a reset component 30', plunger retention protrusions 24', a reset spring 32' on the reset component 30' and a shield locking tab 42' configured to interact with the locking tab protrusion 54' on the safety shield 28. A viewing window 13' may also be provided in the outer housing 12' as shown in FIG. 12. FIG. 13 is an exploded view of the inner components of the embodiment of the device 200 shown in FIG. 12 including the inner housing 14' and safety shield 28'. As in the embodiment described above, an asymmetrical projection 36' is configured to interact with an asymmetrical ramped portion 52' on the reset component 30' during reset of the device 200. Resetting the device 200 unlocks the safety shield 28' and resets the plunger 16' in preparation for a subsequent use of the device 200. When the plunger 16 is in a reset position, the plunger openings 26' interact with the plunger retention protrusions 24' to keep the plunger 16' in a reset position until the safety shield 28' is activated during use of the device 200 as described above. Following use of the device, the safety shield 28 is in an extended, locked position, and the reset component 30' is in a position in which the safety shield locking tab 42' interacts with the locking tab protrusion 54' on the safety shield 28' to maintain the safety shield 28' in the extended, locked position until the device is reset.

FIG. 14A-14B include perspective views of another embodiment 300 of a resettable shield-activated training device including an outer housing 15 having an access port 70, and a safety shield locking tab 42 accessible through the access port 70. In this non-limiting embodiment, the safety shield locking tab 42 can be released from the safety shield 28 to unlock the safety shield by manipulation of the safety shield locking tab via the outer housing 15. In another, non-limiting embodiment, a reset tab projection may extend from the safety shield locking tab 42, which may be accessible to a user through the access port 70. The safety shield locking tab 42 may be movable, as shown in FIGS. 14A-B from a first position to a second position to rotate the reset component (not shown in FIGS. 14A-B) to release the safety shield 28 from a locked position to an unlocked position, releasing the contact between the safety shield locking tab 42 and the locking tab protrusion 54 of the safety shield 28 (not shown in FIGS. 14A-B). In one non-limiting embodiment, a rest cap 34 may still be used to exert axial force on the plunger 16 to reset the plunger 16.

Figures 15A, 15B:
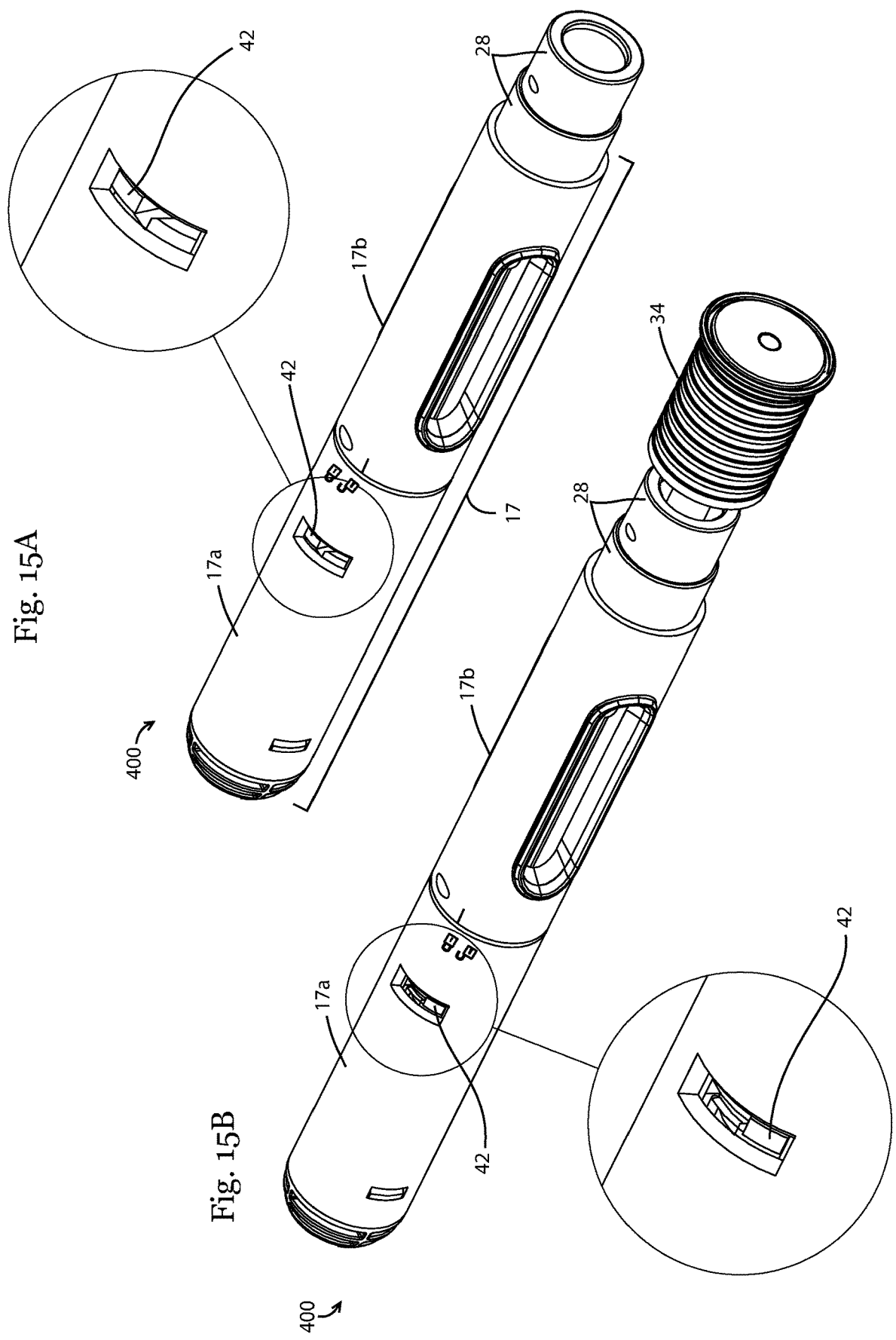
FIGS. 15 A-B include perspective views of another embodiment of a resettable shield-activated injection training device.

In yet another embodiment, in FIGS. 15A-B, perspective views of a resettable shield-activated training device embodiment 400 are shown. The embodiment includes an outer housing 17, a safety shield 28, and a safety shield locking tab 42 which may abut the safety shield 28 in a non-limiting embodiment, to lock the safety shield 28 in an extended position after use of the device. The safety shield locking tab 42 may be manipulated to release it from the safety shield 28 to unlock the safety shield by manipulating the outer housing 17. The outer housing 17 may include at least a first portion 17a and a second portion 17b, the first and second portions 17a, 17b, may be rotatable relative to one another. In one embodiment, the first portion 17a may be rotatable relative to the second portion 17b, and in another embodiment, the second portion 17b may be rotatable relative to the first portion 17a. In yet another embodiment, both the first and second portions 17a, 17b are each rotatable relative to one another. Rotation of one or more of these portions as described serves to unlock the safety shield 28 from a locked position, to an unlocked, or released position, for example, to reset the device 400 for a subsequent use.

In one non-limiting embodiment, a method of using a resettable shield-activated training device embodiment described herein includes pressing the device against a target area of a user such that the safety shield is in contact with the target area. By pressing the safety shield against the target area with sufficient force, the safety shield is retracted into the device, and the device is actuated. The plunger moves to the distal end of the device to simulate an injection. Resetting of the device may occur as described herein, in one example, resetting the device may include insertion of a portion of a reset cap 34 including a reset rod into the distal end of the device, providing an axial force to the plunger, to move the plunger toward the proximal end of the device, to release the safety shield from a locked position to an unlocked position and reset the plunger to a pre-fired position. In another embodiment, reset of the device may occur by manipulating a reset tab or a safety shield locking tab manually, externally, from outside the outer housing. This may be accomplished via an access port in the outer housing. Movement of the tab from a first position to a second position may serve to unlock the safety shield from a locked position to an unlocked position. Reset of the plunger may occur by insertion of a reset rod or reset cap having a reset rod into the distal end of the device and applying an axial force on the plunger to move the plunger toward the proximal end of the device to return the plunger to its pre-fired position.

In an alternative embodiment, unlocking the safety shield may occur by manipulation of the outer housing. In one, non-limiting example, the outer housing may include two or more components that may be rotatable relative to one another as described herein. By rotation of one or more of the rotatable components of the outer housing, the safety shield may be unlocked. The rotation of the outer housing component(s) may rotate the safety shield locking tab to release it from its interaction with the safety shield, such that the safety shield may be unlocked. A reset rod or reset cap including a reset rod may be inserted into the distal end of the device to exert axial force on the plunger to reset the plunger to its pre-fired position.

Certain embodiments herein have been described to include an outer housing and an inner housing; however, in alternative embodiments, the device is not limited to having two housings, the device may include only one housing, and features of both housings may be provided on the sole housing of the device. In further embodiments of the device, there may be more than two housings, for example.

While one or more embodiments of the present invention have been shown and described herein, such embodiments are provided by way of example only. Variations, changes and substitutions may be made without departing from the invention herein. Accordingly, it is intended that the invention be limited only by the spirit and scope of the appended claims. The teachings of all references cited herein are incorporated in their entirety to the extent not inconsistent with the teachings herein.

What is claimed is:

1. A resettable shield-activated injection training device, comprising:
   an outer housing comprising a proximal end and a distal end;
   a plunger slidable relative to the outer housing between a retracted position and an extended position;
   a safety shield comprising an extended locked position, an extended unlocked position, and a retracted position, the safety shield being slidable relative to the outer housing between the extended locked position or the extended unlocked position, and the retracted position;
   a rotatable reset component having axial and radial movement, said reset component configured to interface with the safety shield to lock the safety shield in the extended locked position following use of the device, and
   a reset cap, said reset cap comprising a reset surface to interface with a distal end of the plunger and apply an axial force on the plunger toward the proximal end of the outer housing to rotate the reset component, release the safety shield from a locked position to an unlocked position, and reset the device to a pre-use position.

2. The resettable shield-activated injection training device of claim 1, wherein an application of an axial force on the plunger toward the proximal end of the outer housing rotates the reset component, unlocks the safety shield and resets the device.

3. The resettable shield-activated injection training device of claim 2, wherein the plunger comprises one or more plunger rail portions and the rotatable reset component comprises one or more notched portions on its inner surface, wherein the notched portions are configured to receive the plunger rail portions, wherein movement of the plunger rail portions within the notched portions allow movement of the plunger toward the proximal end of the outer housing.

4. The resettable shield-activated injection training device of claim 1, wherein an application of axial force on the plunger toward the proximal end of the outer housing moves the plunger toward the proximal end of the outer housing to reset the plunger.

5. The resettable shield-activated injection training device of claim 1, wherein the reset component comprises a safety shield locking tab configured to mechanically interact with the safety shield, to lock the safety shield in an extended position.

6. The resettable shield-activated injection training device of claim 5, wherein rotation of the reset component to unlock the safety shield releases the safety shield locking tab from the safety shield.

7. The resettable shield-activated injection training device of claim 5, wherein the safety shield locking tab can be released from the safety shield to unlock the safety shield by manipulation of the safety shield locking tab via the outer housing.

8. The resettable shield-activated injection training device of claim 5, wherein the safety shield locking tab can be released from the safety shield to unlock the safety shield by manipulation of the outer housing.

9. The resettable shield-activated injection training device of claim 8, wherein the outer housing comprises a first portion and a second portion rotatable relative to one another, wherein the manipulation of the outer housing comprises rotation of the first portion relative to the second portion.

10. The resettable shield-activated injection training device of claim 5, wherein the rotatable reset component comprises a torsion spring, wherein when the torsion spring is released, the rotatable reset component rotates such that the safety shield locking tab abuts the safety shield preventing retraction of the safety shield.

11. The resettable shield-activated injection training device of claim 10, wherein an axial force may be applied to the plunger to reset of the device, wherein the axial force applied loads the torsion spring.

12. The resettable shield-activated injection training device of claim 11, wherein the plunger comprises a plunger rail gap disposed along its surface, configured to allow the reset spring to unload, and the rotatable reset component to rotate until the needle shield locking tab interfaces with the safety shield to lock the safety shield in the extended position.

13. The resettable shield-activated injection training device of claim 1, comprising one or more retention protrusions configured to interact with one or more openings on the plunger to retain the plunger in a pre-fired position until the safety shield is in the retracted position.

14. The resettable shield-activated injection training device of claim 1, wherein the plunger comprises a plunger spring, configured to deliver the plunger toward the distal end of the outer housing when the device is actuated.

* * * * *